United States Patent [19]
Pasula

[11] Patent Number: 6,114,174
[45] Date of Patent: Sep. 5, 2000

[54] IN-VITRO DETECTION OF REACTIONS IN BLOOD TO FOREIGN SUBSTANCES

[75] Inventor: Mark J. Pasula, Palm Beach Gardens, Fla.

[73] Assignee: Signet Diagnostic Corporation, Riviera Beach, Fla.

[21] Appl. No.: 09/155,364

[22] PCT Filed: Mar. 25, 1997

[86] PCT No.: PCT/US97/04849

§ 371 Date: Sep. 25, 1998

§ 102(e) Date: Sep. 25, 1998

[87] PCT Pub. No.: WO97/36169

PCT Pub. Date: Oct. 2, 1997

Related U.S. Application Data

[63] Continuation-in-part of application No. PCT/US96/12629, Aug. 1, 1996.
[60] Provisional application No. 60/001,824, Aug. 1, 1995, and provisional application No. 60/014,060, Mar. 25, 1996.

[51] Int. Cl.[7] .................................................. G01N 27/06
[52] U.S. Cl. .................... 436/63; 73/61.71; 324/71.4; 436/149; 436/150
[58] Field of Search ........................... 436/63, 149, 150; 422/82.02; 73/53.01, 61.71, 61.73; 324/71.4, 605, 613, 614, 691, 692, 701, 713, 714, 729

[56] References Cited

U.S. PATENT DOCUMENTS

4,021,117  5/1977  Gohde et al. .
4,788,155  11/1988  Pasula .
5,376,878  12/1994  Fisher .

*Primary Examiner*—Jan Ludlow
*Attorney, Agent, or Firm*—Cohen, Pontani, Lieberman & Pavane

[57] ABSTRACT

The present invention is a method of detecting reaction in blood caused by the presence of a foreign substance in the blood, comprising the steps of: establishing a potential across a predetermined spatial volume; passing a first portion of the blood through the predetermined spatial volume; substantially continuously measuring the potential across the predetermined spatial volume over a first predetermined period of time; comparing the measured potential with a baseline; and calculating the total volume of solids in the first portion of the blood as a function of a total absolute deviation of the measured potential from the baseline. The same procedure is then followed with a second portion of the blood, after it has been exposed to the substance whose reaction is being determined. The two calculations are then compared, with a positive reaction being indicated when the two measured solid volumes are measurably different. The baselines are preferably dynamic baselines, and are determined with reference to the starting point of a sharp rise in the measured potential.

17 Claims, 4 Drawing Sheets

IN-VITRO DETECTION OF REACTIONS IN BLOOD TO FOREIGN SUBSTANCES

CROSS-REFERENCE TO RELATED APPLICATIONS

This application is a continuation-in-part of my prior filed PCT application, Ser. No. PCT/US96/12629, filed Aug 1, 1996 (the disclosure of which is hereby incorporated by reference), which was itself a continuation-in-part of a prior filed provisional application, Ser. No. 60/001,824, filed Aug 1, 1995.

This application is also a continuation-in-part of my prior filed U.S. provisional application Ser. No. 60/014,060 filed Mar. 25, 1996.

Priority of these applications is claimed herein.

BACKGROUND OF THE INVENTION

The present invention is directed to the field of medical diagnoses, and, more specifically, diagnoses performed by detecting reactions in blood caused by the presence of foreign substances therein.

I refer to this test as the "MRT" Test.

The MRT Test relates to the field of hypersensitivity reactions observed in humans and animals. These reactions can be due to contact with offending substances such as medications, environmental chemicals, foods, carcinogens, food additives, etc.

The MRT Test is an in-vitro assay which indirectly detects the release of mediators in whole blood after it is mixed with a test substance. When a patient's blood reacts with the test substance, intracellular fluids are released, causing the liquid portion of blood to increase, while the total volume of the solids present in the blood decreases. These reactions may be caused by various immunologic and non-immunologic mechanisms.

Accordingly, it is an objective of this invention to provide an in-vitro method which will identify reactions caused by various test substances.

It is also an objective of this invention to identify the volumetric differences in the level of plasma in non-treated blood vs. the level of plasma in treated blood.

It is a further objective of this invention to use this new laboratory method as a unique way to solve the problem of identifying maladies which are otherwise difficult to diagnose.

About blood:

Blood is a liquid that circulates throughout the body using the vascular system and is in contact with practically every cell in the body. Blood delivers oxygen, food and other essential elements to all of our cells. Approximately 50% of blood is a fluid called serum (or plasma). It is a complex mixture of water, various proteins, carbohydrates, lipids, and electrolytes. Small amounts of other substances such as vitamins. Minerals, and hormones are also found in blood. The other 50% of blood is comprised of solids such as erythrocytes (red blood cells: RBC), leukocytes (white blood cells: WBC), and thrombocytes (Platelets).

The white blood cells are a significant part of our body's immune system. The immune system is highly complex and intricate in its design and is responsible for defending against foreign invaders such as bacteria, viruses, and other pathogens. The science of immunology incorporates the study of resistance to infections and the rejections of so called "foreign substances".

Gell and Coombs in their 1962 book, Clinical Aspects of Immunology, have identified various immune mediated hypersensitivity reactions and categorized them as Types I–IV, based upon the mechanics of the reaction. Types I, II. and III are identified as antibody mediated and the fourth one is described as cell mediated.

It is understood that Type I is the most widely occurring hypersensitivity reaction. It involves Mast cells and basophils, which bind IgE through their Fc receptors. After encountering the antigen, the antibody induces degranulation (the destruction of the exterior wall of the cell) and release of mediators.

Type II reactions involve the binding of antigen and antibody on the surface of a cell, generally resulting in the destruction of the cell. As is the case in a Type I reaction, the final outcome of this reaction generates the release of cellular contents (including the release of the mediators).

Type III reactions address the interactions of cells with complexes. Immune complexes, when deposited on tissue, cause complement activation, which in turn attracts polymorphonuclear leukocytes ("polymorphs"). As their normal response, the polymorphs will attempt phagocytosis on the complexes, but in many instances the complexes will be trapped by the tissue, blocking phagocytosis. As a natural course, polymorphs will release inflammatory mediators.

Type IV reactions involve sensitized T-lymphocytes. After the second contact with a specific antigen. T cells release lymphokines, which produces an inflammatory response, and in turn attracts mediator-releasing macrophages.

This is an accepted theory, which generally explains the partial release of cytoplasm and mediators into the blood stream, or upon tissue as a result of such reactions. As these reactions occur, the volumetric level of the plasma will change.

As observed under the microscope, there are two possible reactions triggered by offending substances;

a. release of liquid (substance, cytoplasm and mediators) from cells, causing decrease in solids/liquid volumetric ratio in blood; or b. consumption of liquids, causing increase of solids/liquid ratio in blood.

It appears that at any time human blood can react one way or the other However, it was also observed that usually only one type of reaction takes place at a time.

It is contemplated that similar phenomena takes place by reason of contact with chemical substances such as gases (aerosols, pesticides, gases, cigarette fumes), paints, perfumes, oils, gas, thinners, air fresheners, food additives, drugs, and many other substances.

There is very little scientific explanation why humans and animals react to the above named substances. Some theories suggest a classic allergic reaction, while others state that lack of specific enzymes, helping to neutralize foreign substances, are the reason for those reactions.

In summary, reactions caused by immune, toxic, pharmacological and other mechanisms may cause the release of mediators into the blood stream.

Current methods of diagnosis exist for measuring the degree of reaction a patient's blood may have with a suspected allergen, by measuring the size and number of blood cells in a patient's blood. Such tests are described in my prior U.S. Pat. Nos. 4,614,722; 4,788,155; and 5,147,785, the disclosures of which are herein incorporated by reference. In essence, these patented tests operate by comparing the number and size of cells in a patient's blood before and after exposure to a foreign substance. If there is a significant cellular shift after exposure, then a positive reaction is determined.

These tests, while a significant improvement in the art at the time they were made, have a drawback, in that they do not well measure small differences in cell sizes caused by the described cellular reactions.

Currently, no tests are known which may test for the reaction blood cells have to foreign substances resulting in changes in plasma volume independent of changes in cell size distributions.

OBJECTS AND SUMMARY OF THE INVENTION

Accordingly, it is an object of the invention to provide an improved method of determining cellular reaction caused by foreign substances, which overcomes the drawbacks of the prior art.

It is a further object of the invention to provide an improved method for diagnosing maladies caused by the presence of foreign substances in a patient's blood, by measuring the volume of plasma, or the volume of solids, in a patient's blood before and after exposure to a foreign substance whose effects are under consideration.

Briefly stated, there is provided a method of detecting reaction in blood caused by the presence of a foreign substance in the blood, comprising the steps of: establishing a potential across a predetermined spatial volume; passing a first portion of the blood through the predetermined spatial volume; substantially continuously measuring the potential across the predetermined spatial volume over a first predetermined period of time; comparing the measured potential with a baseline; and calculating the total volume of solids in the first portion of the blood as a function of a total absolute deviation of the measured potential from the baseline. The same procedure is then followed with a second portion of the blood, after it has been exposed to the substance whose reaction is being determined. The two calculations are then compared, with a positive reaction being indicated when the two measured solid volumes are measurably different. The baselines are preferably dynamic baselines, and are determined with reference to the starting point of a sharp rise in the measured potential.

In accordance with these and other objects of the invention, there is provided an in-vitro method for detecting a reaction in blood caused by substances, comprising the steps of: establishing a first potential across a first predetermined spatial volume; passing a first portion of the blood through the first predetermined spatial volume; substantially continuously measuring the first potential over a first predetermined period of time; comparing the measured first potential with a first baseline; calculating the total volume of solids in the first portion of the blood as a first function of a total absolute deviation of the measured first potential from said first baseline; exposing a second portion of the blood to a substance; establishing a second potential across a second predetermined spatial volume; passing the second portion of the blood through the second predetermined spatial volume; substantially continuously measuring the second potential over a second predetermined period of time; comparing the measured second potential with a second baseline; calculating the total volume of solids in the second portion of the blood as a second function of a total absolute deviation of the measured second potential from the second baseline; and comparing the total volume of solids in the second portion of the blood with the total volume of solids in said first portion of blood, whereby a positive reaction is established when the total volume of solids in the second portion of blood differs from the total volume of solids in the first portion of blood by more than a predetermined error factor.

According to feature of the invention, there is further provided an in-vitro method for detecting a reaction in blood caused by substances, comprising the steps of: establishing a first potential across a first predetermined spatial volume; passing a first portion of the blood through the first predetermined spatial volume; substantially continuously measuring the first potential over a first predetermined period of time; comparing the measured first potential with a first dynamic baseline; calculating the total volume of solids in the first portion of the blood as a first function of a total absolute deviation of the measured first potential from the first dynamic baseline; exposing a second portion of the blood to a substance; establishing a second potential across a second predetermined spatial volume; passing the second portion of the blood through the second predetermined spatial volume; substantially continuously measuring the second potential over a second predetermined period of time; comparing the measured second potential with a second dynamic baseline; calculating the total volume of solids in the second portion of the blood as a second function of a total absolute deviation of the measured second potential from the second dynamic baseline; and comparing the total volume of solids in the second portion of the blood with said total volume of solids in the first portion of blood, whereby a positive reaction is established when the total volume of solids in the second portion of blood differs from the total volume of solids in the first portion of blood by more than a predetermined error factor.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

The MRT Test relies in large part upon the performance of the test described in my co-pending PCT application, and reference is made thereto for a more complete understanding of the mechanics of the testing being done. The following is presented for convenience of reference.

Description of the MRT procedure:
1. Supplies and Instrumentation.
2. Blood collection and test preparation.
3. Testing.

4. Results.
1. Supplies and Instrumentation.
   (supplies and instrumentation may vary to some extent and depend on the type of testing instrument employed for the MRT Test. In this case I have chosen the semi-automated STS100 manufactured by Signet Diagnostic Corporation, and the following description is made with that device as a reference).
   100 µl–500 µl adjustable multi pipette
   10–20 ml dispenser, e.g. an Oxford pipetor to dispense the electrolytic solution mixed with a lysing agent
   body temperature incubator, e.g. by Precision Scientific
   60–100 rpm rotator, e.g. by Roto Mix
   70 ml blood dilution vial with diluent
   10 lysing reagent (as described in my prior patents) 8 ml vial
   testing cuvettes with reagents. The reagents are dried and diluted food extracts, e.g. by ALK or Bayer. Their concentration varies from 1:400 to 1:2,000.000 depending upon their toxicity
   isotonic (electrolytic) solution, e.g. Osmocel Isotonic Solution by Hematronic
   Apparatus, STS100 or STS200 made by Signet Diagnostic Corp.
2. Blood collection and test preparation.
   I. Draw 5–10 ml of blood into a vacutainer containing 3.8% citrate solution without the "buffer" (citric acid, which may, itself, be an allergen).
   II. Pour collected blood into the blood dilution vial.
   III. Using the multi-pipette, transfer 700 µl of diluted blood into panels of control and sample cuvettes (each panel will have at least one control cuvette and at least one sample cuvette). Control samples contain no reagent. Test samples contain a small amount of a substance being evaluated, the "reagent". The control sample serves as a fingerprint of the patient's blood. The test sample provides information related to the reaction of the tested substance to the reagent being tested.
   IV. After transferring blood to all tested samples, mix all cuvettes and cap them.
   V. Place tray on the top of the rotator in the incubator. Turn the rotator on.
   VI. Incubate for 30 minutes at body temperature.
   VII. Remove from incubator and follow by 30 minutes room temperature incubation. Total of 60 minutes incubation.
3. Testing:
   The MRT Test, the new proprietary laboratory method, can be described in the following fashion:
   a. Incubation of predetermined amount of blood in its native form which serves as the fingerprint for the test.
   b. Incubation of a predetermined amount of blood mixed with tested substance (at least 1 test sample).
   c. Measure total volume of liquid and/or solids in native blood sample by means of the method described in my prior PCT application.
   d. Measure total volume of liquid and/or solids in the mixture of blood and tested substance sample. If in step "c", you measure liquids, then do so here. Likewise with solids, so that comparisons may be made "like-to-like".
   e. Repeat step "d" for each tested substance. This may be done in parallel, i.e. several test measurements taken at the same time, or one after another. The parallel arrangement, however, is the most time-effective.
   f. Identify volumetric differences of liquid volume and or solid volume between native blood sample and the tested blood sample.
   g. Prepare the results identifying the measured volumetric differences.
   h. Identify the positive and negative reactions, by noting which reagents produced a measurable reaction, i.e. one greater than the standard deviation expected for the test, calculated in known fashion.

The in vitro trend in the field of allergy, is to measure levels of specific immunoglobulins and detect the presence of individual mediators. In my research studies, I have identified that more then one mechanism may be employed in adverse reactions to foreign substances. By measurement of volumetric differences in plasma we may deliver more comprehensive answers.

Figure 1:
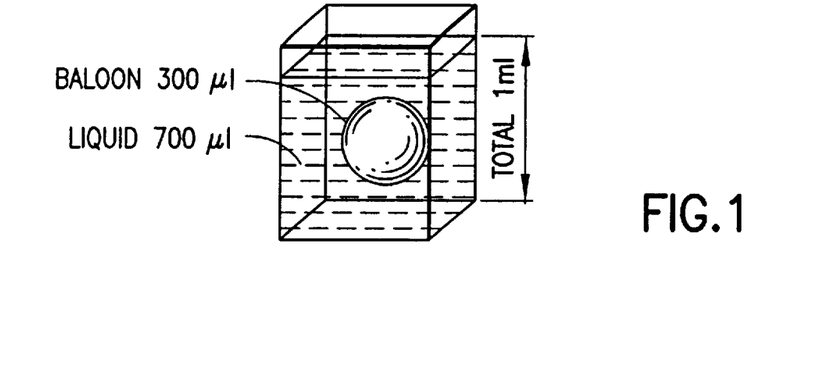
FIG. 1 illustrates an idealized particle (balloon) having a volume of 300 $\mu$l, in a unit volume of 1 ml of a suspension, leaving a liquid volume of 700 $\mu$l.
Figures 2, 3:
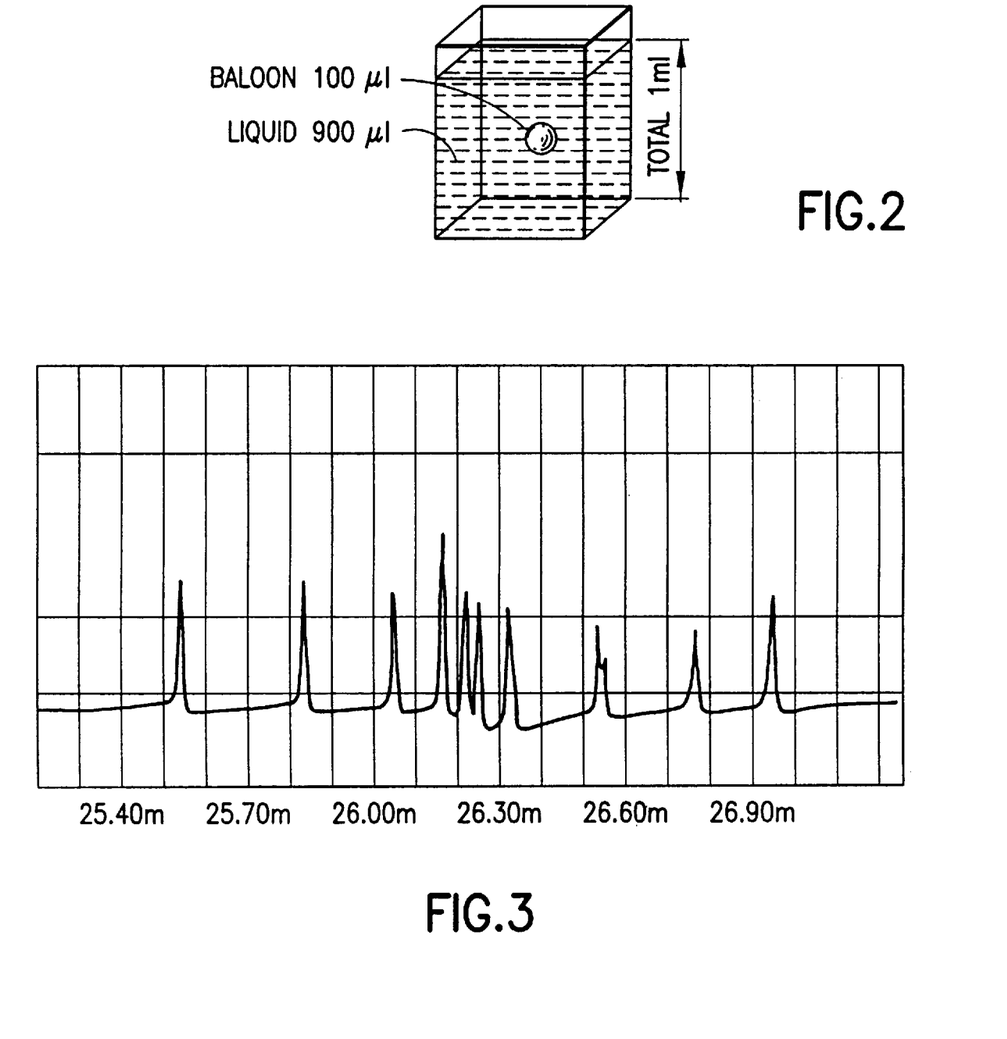
FIG. 2 illustrates an identical unit volume of 1 ml (not drawn to scale), in which the particle has a volume of only 100 $\mu$l, and the liquid a resultant volume of 900 $\mu$l.
FIG. 3 illustrates an actual oscilloscope reading of a series of particles being measured as they pass through the electromagnetic field under observation.

FIG. 1 represents a small cuvette containing 1 ml of heterogeneous fluid. The liquid portion is equivalent to 700 µl. The balloon filled with black ink has an equivalent volume of 300 µl. Note that for purposes of measurement the balloon would be considered as a solid entity. FIG. 2 represents the same cuvette after the balloon has released 200 µl of its ink into the external liquid. The Total volume of suspension is still 1 ml. The volume of the liquid has increased to 900 µl and the volume of the balloon has decreased to 100 µl.

This example illustrates how human blood cells react in the body. When the reacting substance is introduced to the blood, it triggers a series of complex reactions. In the end, the intracellular fluids will be released into the plasma, changing the original ratio of solids to liquid. The ratio is the key for identifying the malady (the intracellular liquids contain the mediators causing the clinical symptomology), but the ratio can be determined easily from a measurement of either the solid or the liquid volume per unit volume of the blood suspension.

There are many instruments widely used in the field of hematology, which employ the electrical resistance principal of counting and sizing. It is based on the fact that human cells are poor conductors of electricity, while plasma is a good conductor.

The basic apparatus is shown in my prior PCT patent application, and includes an aperture tube in which the blood suspension is drawn into an orifice and along an aperture. An electromagnetic field is imposed upon the aperture, and the blood suspension is drawn through the field. Since the liquid of the suspension is essentially homogeneous, and conductive, while the blood cells are resistive, with their resistivity varying with their size, the size of the blood cells passing through the aperture may be calculated by measuring the perturbation of the field as the particles pass therethrough.

As cells pass through the aperture, the change of voltage that occurs is registered by the instrument. All instruments known prior to my inventive method (described in my co-pending PCT application) measure the peak of the impulse produced by the resistance of cell. A specific threshold is set during calibration which controls the minimum level of signal detection. This in turn lowers the presence of the electronic "noise". When the voltage change exceeds the level of the threshold, the instrument will identify the peak of that impulse. This method is commonly called the "impedance" or "peak detection method".

To conduct the MRT Test, one needs a very precise measurement of the volumes of liquids and solids in tested fluid. Common hematology instrumentation does not posses high precision for volumetric measurement and even though they are accepted in the hematology field, they cannot register very small volumetric changes occurring in cells during reactions. For that reason I developed my new (PCT)

patent pending method for measuring the volume of solids in a suspension. Like many hematology instruments, it employs the principal of resistance, illustrated by Ohm's Law:

$$V_{VOLTAGE} = I_{CURRENT} \times R_{RESISTANCE}$$

The new method does not adhere to the standard peak detection. It continuously measures the flow of volume of liquid and solids in the tested liquid.

The actual measurement will appear, if taken graphically, to be the same as an oscilloscope reading in time and resembles a continuous electrical wave signal (see the actual computer printout identified as FIG. 3).

The series of spikes represent particles causing small disturbances in the electrical field. The longer and higher the pulse, the greater the volume of the particle (See printout identified as FIG. 4).

Figure 5:
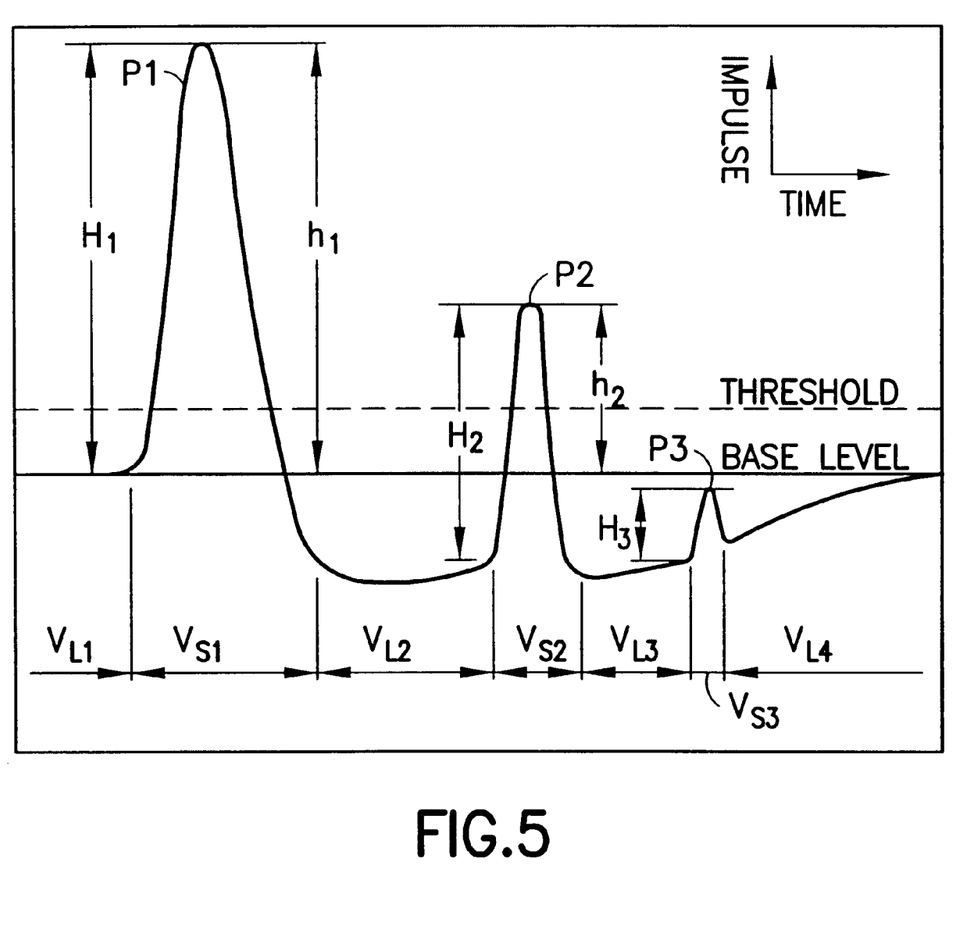
FIG. 5 shows a smoothed curve showing three particles passing through the electromagnetic field being measured.

Accordingly, a smaller particle will create a shorter disturbance of a smaller magnitude, and a larger particle will cause a longer disturbance of a greater magnitude. There is a definite relationship between the length, height and volume of the tested particle. Since the STS200 apparatus measures with a frequency better then 1 MHZ, it is easy to identify the relationship between the size of the particle and the time it will need to pass through the orifice. FIG. 5 explains how the MRT measurement works and how it differs from the Coulter Method.

The description of the (Prior Art) Coulter Method.

A disturbance caused by particle "P1" produces the spike with the peak high's marked "$h_1$". It is measured from the base level up to the peak of the signal. After the particle travels the length of the aperture, the measured signal experiences a "bounce" in which the measured signal goes below the original baseline, and gradually goes on an upward gradient towards the original baseline. But a subsequent particle may often enter the aperture before the "bounce" is over. For example, in FIG. 5, second particle "P2" starts its disturbance below the static base level. The height of $h_2$ is measured from the baseline and clearly shows, that the result is not very accurate since the true disturbance commences below that level. The third particle (P3) is a platelet and its electrical disturbance is entirely below the base level, due to the large "bounce" caused by P2, and so is invisible to the instrument.

Disadvantages:

The lower size limit of particles which may be measured is determined by the static noise threshold established during calibration. The upper size limit is related to the physical size of the aperture. A major problem associated with electric resistance particle counting and sizing becomes evident when attempts are made to evaluate two dissimilar particle sizes at the same time using the same aperture, e.g. simultaneous measurement of erythrocytes and platelets. After cells pass through the orifice, some re-enter the electrical field with the pulse resembling the size of platelets. Threshold and electrical "noises" are also a substantial problem. A specific constant threshold is set during the calibration which controls the minimum level of signal detection. This in turn lowers the presence of the electronic "noise". When the voltage change exceeds the level of the threshold, the instrument will identify the peak of that impulse. This is the basis of the peak detection method.

Description of the MRT (Ribbon) Method.

According to the inventive method, an instrument continuously measures the level of the electromagnetic field as the suspension flows through the orifice, regardless of the level of the signal. Examples of the signal measurement are represented by "H" in FIG. 5. Compare this reading with the prior art method represented by "h". After the particle "P1" passes through the orifice, the signal dips down below the threshold and the baseline. The Coulter method stops the measurement when the signal goes below the threshold level, but the new measurement follows the signal and measures the time of impulse "P1" which is "$V_{s1}$", the time it takes for particle P1 to stop disturbing the measured signal. The time is measured as the duration of the interval commencing when the gradient of the curve begins to indicate the presence of a particle until the measured signal returns to its original level. The presence of the particle is indicated when the gradient increases for a predetermined period, preferably corresponding to at least three consecutive measurement clock cycles.

As the particle leaves the orifice, the instrument measures time identified as "$V_{L2}$". This is the time it takes fluid to pass through the orifice. As we approach the point "$V_{S2}$", another particle "P2" enters the orifice. The signal is still below the static threshold and the static baseline, but the STS100 instrument recognizes the condition and begins to measure the solid particle. This establishes a dynamic baseline, which is defined as the value of the measured signal when the gradient of the curve begins to increase. The height of the perturbation of the signal is therefore measured as $H_2$, from the dynamic baseline, rather than from the static baseline as shown by $h_2$. This more accurately reflects the true size of the perturbation of the signal, and therefore the size of the particle.

The duration of the signal identified as "$V_{L2}$" is another important part of the measurement. If we look at signal "P3". it is evident, that the whole impulse is contained below the baseline. The volume of the solid, identified by time "$V_{s3}$" arid measured from the dynamic baseline becomes part of the measurement. The MRT Ribbon Method thus correctly measures all particles suspended in the electrolytic solution. There is a definite relationship between the length, height and volume of the tested particle. Since the STS200 apparatus measures with a frequency greater then 1 MHZ, it is easy to identify the relationship between the size of the particle and the time it will need to pass through the orifice. Also the flow of fluid is identified.

It has been determined, as well, that the gradient of the curve on the upward slope of the curve when a particle is present also varies with the size of the particle, larger particles having a steeper slope. The exact relationship depends upon the configuration of the system, and may be determined with some minor experimentation depending upon the parameters of the equipment being used. Thus, the gradient may also be used to calculate the size of the particles.

Figure 4:
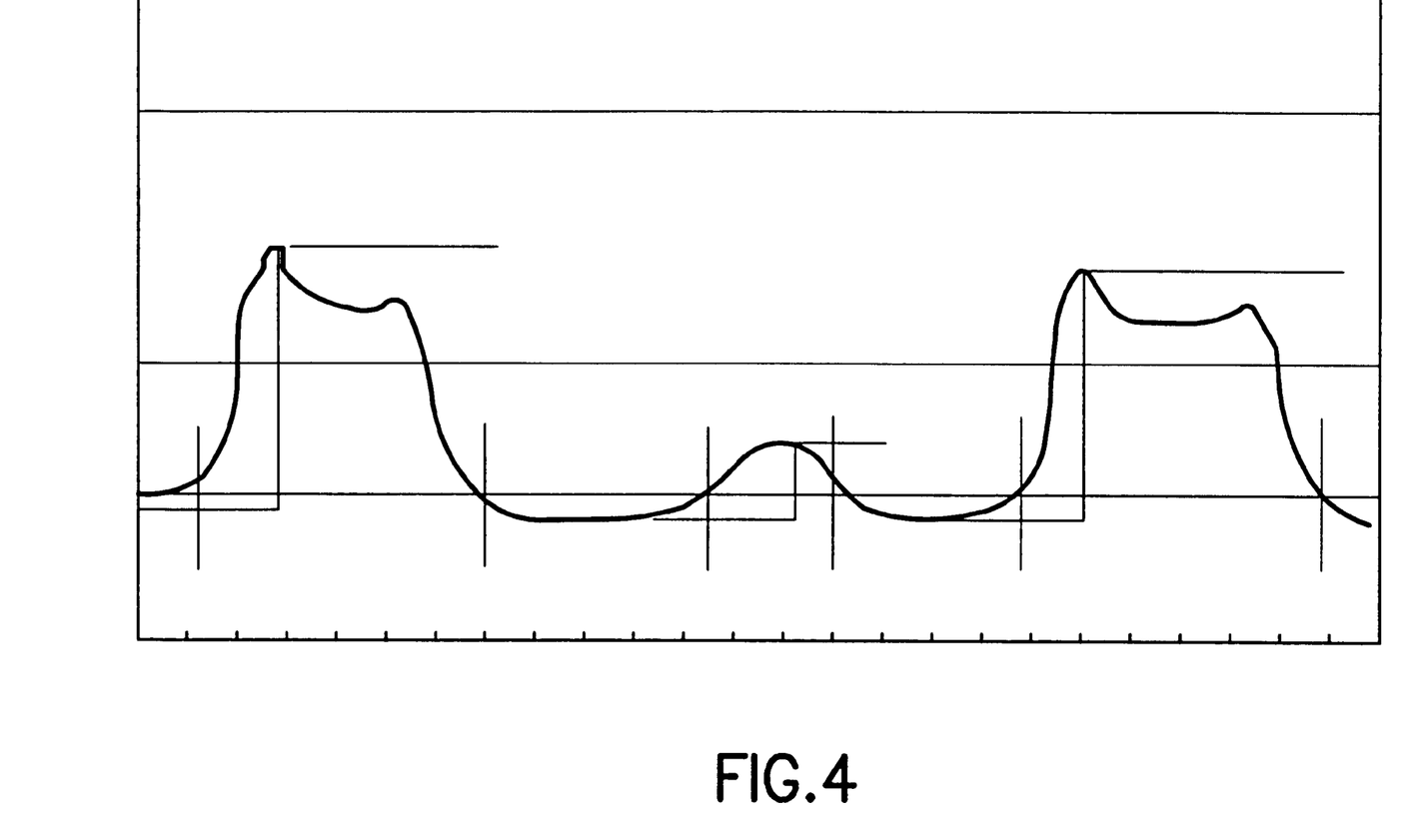
FIG. 4 shows a close up of some oscilloscope readings such as depicted in FIG. 3.

One point should be made about correction of the rough signal shown in FIG. 4. As described in my earlier PCT application, the actual size of a particle is represented by the "trough" between the peaks of the measurement curve shown on either the right or left of the figure. The value of the trough is the one selected to represent the corrected height of the curve.

Figure 6:
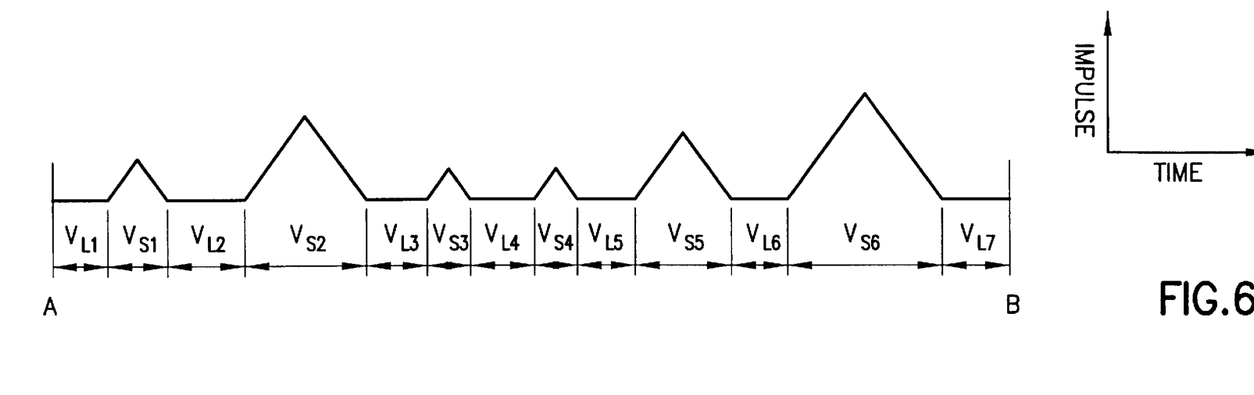
FIG. 6 shows an idealized representation of a series of particles passing through the electromagnetic field.

The flow of fluid is also identified. FIG. 6 graphically represents how the STS200 identifies the volume of solid and the volume of liquid.

Letter A represents the beginning of the test.

$V_L$=Volume in time in which an instrument measures the liquid $V_S$=Volume in time in which an instrument measure the solid particle. Total measured volume:

$V_T = V_{LT} + V_{ST}$ where $V_{LT} = V_{L1} + \ldots + V_{Ln}$ and $V_{ST} = V_{S1} + \ldots + V_{sn}$ During the measurement, the fluid flows through the orifice. The liquid portion is characterized by the flat impulse line and the solid portion is characterized as the visual disturbance in the flat impulse signal. As the 1 ml (volume of 1 ml is given only as an example) of diluted blood passes through the orifice, the computer software program quantifies the cumulative volume of liquid and cumulative volume of solids in accordance with the rules established, here.

There are at least three different ways of data collection and results presentation:

1. Measure 1 ml (or other predetermined volume) of the diluted blood sample. Calculate the total volume of all solids and subtract them from 1 ml. From the difference, the total volume of liquid in the 1 ml of blood suspension will be given and the volume of liquids in the control and test sample can be compared; or
2. Compare only the total volume of solids in the two samples; or
3. Compare the ratio of solids to liquids (or liquids to solids) in the two samples.

Each of these measurements is essentially the same, and any one (or more) of them may be used at the convenience of the user, as desired.

Step By Step Testing Procedure:

For purposes of visualization I will describe the MRT procedure conducted on the STS200 continuous flow instrument.

After proper test preparation (see section 2), take incubated cuvette identified as a "control" and gently mix. Draw 100 $\mu$l of diluted blood and transfer it into empty cuvette. You will have two control cuvettes, one containing 600 $\mu$l and another 100 $\mu$l of diluted blood. Dispense 10 ml of isotonic solution into each cuvette. Additionally add 100 $\mu$l of lysing agent to the cuvette containing 600 $\mu$l of suspended blood. Place both cuvettes on the stage and start the test run. An instrument will measure the volume of one ml of the suspended blood in both cuvettes one after another and will display detailed information on how many femtoliters (fl) of liquid is present in one milliliter of suspended whole blood. The next step repeats the preparation process of the sample cuvette. Draw 100 $\mu$l of diluted blood from the incubated sample test cuvette. Transfer it into the empty cuvette. Dispense 10 ml of isotonic solution into each cuvette. Add 100 $\mu$l of lysing agent into the cuvette containing 600 $\mu$l of suspended blood. Place both cuvettes on the stage and run the test. Repeat the cycle for each additional sample tested. Results will be calculated from the information obtained from all samples, by comparing the total volume of liquid of control sample to the total volume of liquid of the substance sample. We will obtain two results from each substance. One sample will give us information on the activities of the Red Blood Cells (RBC) and another sample will inform us on reactions of all other then RBC blood components in presence of tested substance. It is not mandatory to conduct the MRT Test in this exact fashion. Per individual need, one can conduct the partial test obtaining results from the first or the second solution only.

4. Results

The computer will establish the volumetric baseline of the plasma (liquid) present in one cubic millimeter of control blood sample. Once the baseline is established, the actual volume of plasma present in each milliliter of each blood sample will be calculated and compared against the actual volume of plasma in the control sample. If liquid volume in the control sample significantly varies from liquid volume in the test sample, the tested substance is identified as reacted. A significant reaction would be one greater than could be attributed to the known instrumentation error plus the standard deviation for similar measurements. Any difference of less than that amount would not necessarily indicate a positive reaction, since it could be attributed to statistical or instrumentation error.

Figure 7:
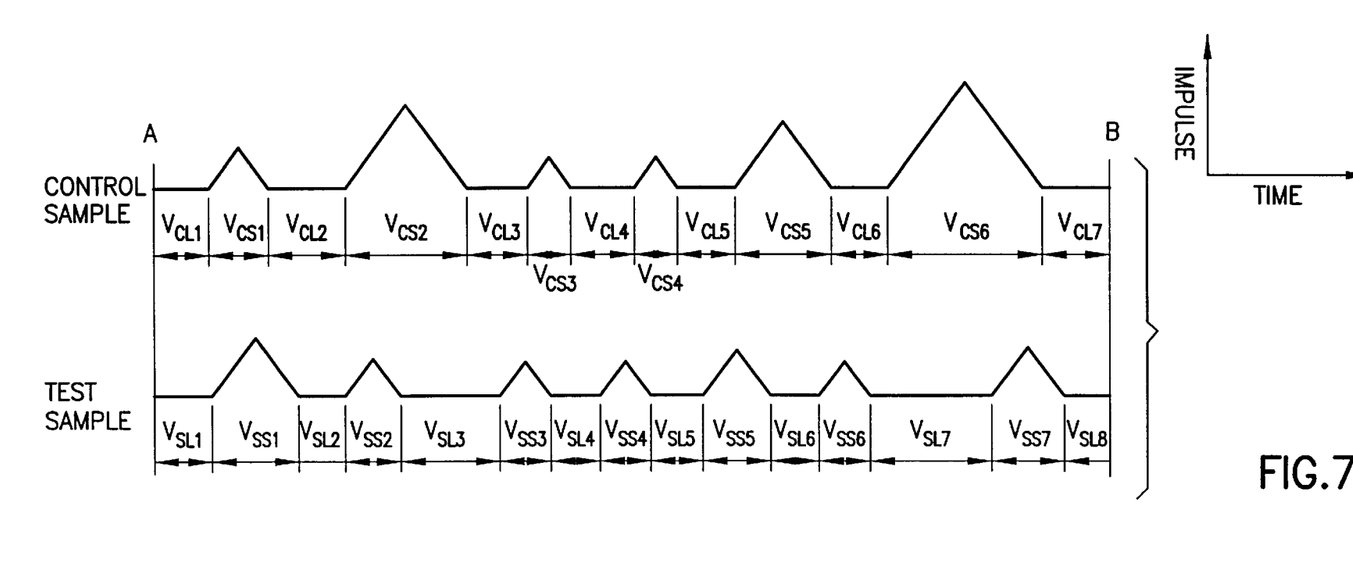
FIG. 7 shows an idealized representation of a comparison of test and control sample readings as the particles pass through the electromagnetic field.

FIG. 7 portrays the measurement of the blood sample distribution of the Control and Test Samples. The differences between the distribution patterns would be due to the exposure of the Test Sample to the tested substance.

The computer program will calculate the variation and save it as the results data. Interpretation of results will be based on the standard deviations and other generally accepted laboratory methods of results interpretation.

It will be appreciated by those of ordinary skill in the art that the measurements of the electromagnetic signal described above may be made of either the voltage or the current, since it is the resistance within the aperture which changes and the imposed field is otherwise constant.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An in-vitro method for detecting a reaction in blood caused by substances, comprising the steps of:

establishing a first potential across a first predetermined spatial volume;

passing a first portion of said blood through said first predetermined spatial volume;

substantially continuously measuring said first potential over a first predetermined period of time;

comparing said measured first potential with a first baseline;

calculating the total volume of solids in said first portion of said blood as a first function of a total absolute deviation of said measured first potential from said first baseline;

exposing a second portion of said blood to a substance;

establishing a second potential across a second predetermined spatial volume;

passing said second portion of said blood through said second predetermined spatial volume;

substantially continuously measuring said second potential over a second period of time;

comparing said measured second potential with a second baseline;

calculating the total volume of solids in said second portion of said blood as a second function of a total absolute deviation of said measured second potential from said second baseline; and comparing said total volume of solids in said second portion of said blood with said total volume of solids in said first portion of blood, whereby a positive reaction is established when said total volume of solids in said second portion of blood differs from said total volume of solids in said first portion of blood by more than a predetermined error factor.

2. The method of claim 1, wherein at least one of said first and said second substantially continuous measured potentials forms a curve, and at least one of said first and second functions is an integral of said curve, so that the total volume of solid material measured thereby is a third function of the total area under said curve.

3. The method of claim 1, wherein at least one of said first and second substantially continuous measured potentials forms a curve, and at least one of said first and second functions includes determining a gradient of said curve.

4. The method of claim 3, wherein said at least one of said first and second functions further includes identifying the presence of a solid in the predetermined spatial volume measured thereby by comparing changes in said gradient over time.

5. The method of claim 4, wherein the presence of a solid in said predetermined spatial volume is identified when said comparison of changes in said gradient shows that said gradient has remained substantially constant for a third predetermined period of time.

6. The method of claim 5, wherein said substantially continuous measurement of said potential comprises a series of discrete measurements.

7. The method of claim 6, wherein said series of discrete measurements comprises at least one million measurements per second.

8. The method of claim 7, wherein said third period of time is no fewer than three of said discrete measurements.

9. The method of claim 5, wherein the presence of a solid to be measured is indicated by a sharp increase in said gradient.

10. The method of claim 9, wherein at least one of said first and second baselines is a dynamic baseline located at the value of said measured potential at a point on said curve immediately prior to said sharp increase in said gradient, and said volume of said solid is measured from said dynamic baseline.

11. The method of claim 10, further comprising the step of storing said volume of each said solid.

12. The method of claim 11, further comprising the step of summing the volume of all measured solids, thereby measuring the total volume of all solids in said blood.

13. The method of claim 3, wherein said at least one of said first and second functions includes:

storing the value of said curve at a point when said gradient of said curve increases for more than a fourth predetermined time interval; and measuring a time duration commencing when said gradient increases for more than said fourth predetermined time interval until said value of said curve returns to said value.

14. The method of claim 13, wherein said comparison of said potential to said baseline yields a height of said curve; and said at least one of said first and second functions is derived from at least one of said time duration, said gradient of said curve and said height of said curve.

15. The method of claim 1, wherein said first and second functions are identical.

16. An in-vitro method for detecting a reaction in blood caused by substances, comprising the steps of:

establishing a first potential across a first predetermined spatial volume;

passing a first portion of said blood through said first predetermined spatial volume; substantially continuously measuring said first potential over a first predetermined period of time;

comparing said measured first potential with a first dynamic baseline;

calculating the total volume of solids in said first portion of said blood as a first function of a total absolute deviation of said measured first potential from said first dynamic baseline;

exposing a second portion of said blood to a substance;

establishing a second potential across a second predetermined spatial volume;

passing said second portion of said blood through said second predetermined spatial volume;

substantially continuously measuring said second potential over a second predetermined period of time;

comparing said measured second potential with a second dynamic baseline;

calculating the total volume of solids in said second portion of said blood as a second function of a total absolute deviation of said measured second potential from said second dynamic baseline; and comparing said total volume of solids in said second portion of said blood with said total volume of solids in said first portion of blood, whereby a positive reaction is established when said total volume of solids in said second portion of blood differs from said total volume of solids in said first portion of blood by more than a predetermined error factor.

17. The method of claim 16, wherein said first and second functions are identical.

* * * * *